(12) United States Patent
O'Ruanaidh et al.

(10) Patent No.: US 8,372,006 B1
(45) Date of Patent: Feb. 12, 2013

(54) METHOD FOR DETECTING AND LOCATING A TARGET USING PHASE INFORMATION

(75) Inventors: Joseph O'Ruanaidh, Hamilton, NJ (US); Christopher J. Vecchio, Philadelphia, PA (US); Edmond Rambod, Los Angeles, CA (US)

(73) Assignee: Quantason, LLC, Los Angeles, CA (US)

( * ) Notice: Subject to any disclaimer, the term of this patent is extended or adjusted under 35 U.S.C. 154(b) by 275 days.

(21) Appl. No.: 12/802,867

(22) Filed: Jun. 16, 2010

(51) Int. Cl.
*A61B 8/00* (2006.01)
(52) U.S. Cl. ........................................ 600/437; 382/128
(58) Field of Classification Search .......... 600/407–429, 600/437–469; 382/128–132
See application file for complete search history.

(56) References Cited

U.S. PATENT DOCUMENTS

| 5,921,928 | A | | 7/1999 | Greenleaf | |
|---|---|---|---|---|---|
| 6,130,641 | A | * | 10/2000 | Kraeutner et al. | 342/179 |
| 7,756,246 | B2 | * | 7/2010 | Mikami et al. | 378/37 |
| 8,109,878 | B1 | * | 2/2012 | O'Ruanaidh et al. | 600/443 |
| 2003/0004413 | A1 | * | 1/2003 | Inoue et al. | 600/436 |
| 2004/0220465 | A1 | * | 11/2004 | Cafarella | 600/407 |
| 2005/0020921 | A1 | * | 1/2005 | Glassell et al. | 600/463 |
| 2008/0242979 | A1 | * | 10/2008 | Fisher et al. | 600/427 |
| 2009/0088637 | A1 | * | 4/2009 | Mikami | 600/443 |
| 2009/0234229 | A1 | * | 9/2009 | Mikami et al. | 600/445 |
| 2009/0247869 | A1 | * | 10/2009 | Rambod et al. | 600/437 |
| 2009/0264758 | A1 | * | 10/2009 | Fujita et al. | 600/443 |
| 2009/0290679 | A1 | * | 11/2009 | Mikami et al. | 378/37 |
| 2010/0016717 | A1 | * | 1/2010 | Dogra et al. | 600/437 |
| 2010/0022881 | A1 | * | 1/2010 | Fujita et al. | 600/445 |
| 2010/0030078 | A1 | * | 2/2010 | Mikami | 600/443 |

OTHER PUBLICATIONS

J.J.K. O'Ruanaidh, Numerical Bayesian Methods Applied to Signal Processing (Springer Verlag, 1996).
W. Press et al., Numerical Recipes in C (Cambridge Press, 1992), 2nd ed.
A. Quinn, The performance of Bayesian estimators in the super-resolution of signal parameters, IEEE International Conference on Acoustics, Speech and Signal Processing (1992).

* cited by examiner

*Primary Examiner* — Sanjay Cattungal
(74) *Attorney, Agent, or Firm* — Thomas I. Rozsa

(57) ABSTRACT

The present invention is a method for detecting and locating a target using phase information obtained from an array of microphones or other sensors.

10 Claims, 2 Drawing Sheets

US 8,372,006 B1

METHOD FOR DETECTING AND LOCATING A TARGET USING PHASE INFORMATION

BACKGROUND OF THE INVENTION

1. Field of the Invention

The present invention relates to the field of diagnostic medical imaging in general and the field of breast cancer screening by ultrasound in particular.

2. Description of the Prior Art

Closest Prior Art:

1. United States Patent Application #20090247869, Rambod; Edmond; et al. Oct. 1, 2009, "Application of image-based dynamic ultrasound spectrography (IDUS) in detection and localization of breast micro-calcifications."
2. J. J. K. Ó Ruanaidh and W. J. Fitzgerald, Numerical Bayesian Methods Applied to Signal Processing (Springer Verlag, 1996).
3. W. Press, S. Teukolsky, W. Vetterling, and B. Flannery, Numerical Recipes in C (Cambridge University Press, 1992), 2nd ed.
4. A. Quinn, "The performance of Bayesian estimators in the superresolution of signal parameters," in "IEEE International Conference on Acoustics, Speech and Signal Processing," (1992).
5. U.S. Pat. No. 5,921,928, Greenleaf, et al., Jul. 13, 1999, "Acoustic force generation by amplitude modulating a sonic beam."

SUMMARY OF THE INVENTION

The present invention is a method for detecting and locating a target using phase information obtained from an array of microphones or other sensors.

The basic concept behind the present invention is to introduce a device that includes a transmitting and stimulating ultrasound transducer (probe) and a multiplicity of sensors at given locations around or adjacent to a human breast. The sensors can be arranged in the form of a ring, can be in any random arrangement of locations, or can be positioned in specifically selected locations. The sensors can all be located in the same plane or in a 3 dimensional configuration around a human breast. An ultrasound transducer generates certain stimulating signals which are transmitted to the breast and which, in presence of a microcalcification or other target, will result in reflected, demodulated, reradiated and scattered signals. These signals will travel away from the microcalcification and toward a location or locations whereby the various sensors are located.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
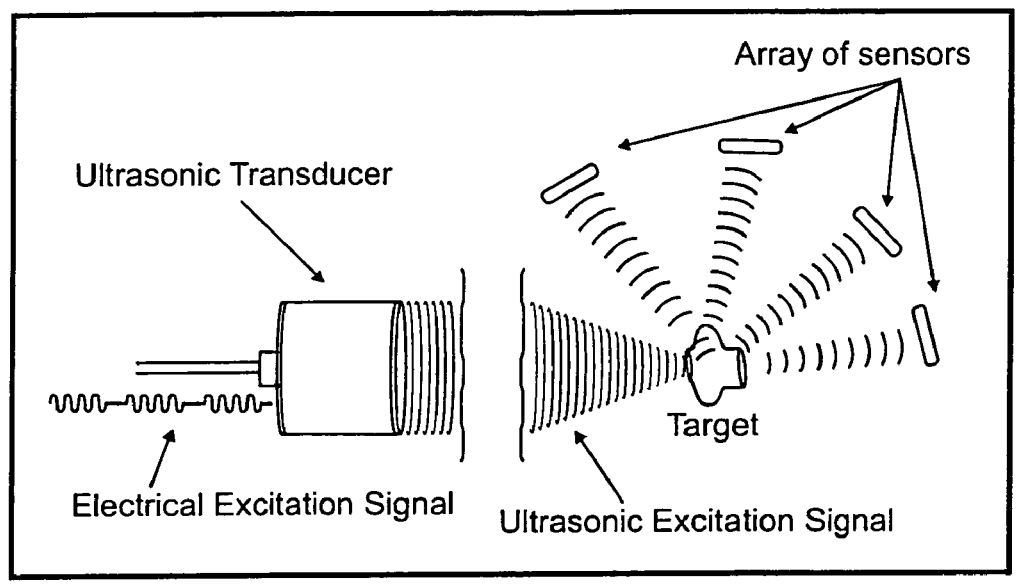
FIG. 1 is an ultrasonic transducer emitting a signal that impinges on a target. The signal energy is reflected, demodulated, reradiated, and scattered and subsequently received by a number of sensors.

FIG. 1 shows an ultrasonic transducer emitting a signal that impinges on a target within tissue. The signal energy is reflected, demodulated, reradiated, and scattered and subsequently received by a multiplicity of sensors. A phase analysis of the information received by each individual sensor can be carried out in order to determine the location of the radiating target. Because each sensor is located at a slightly different distance from the target, the different distances result in different phase shifts in the signals received by each individual sensor. The phase shifts are proportional to the distance between each individual sensor and the target. The phase shifts correspond to the time between the generation of the ultrasonic stimulation signal and the reception by the sensor of a signal reflected, demodulated, reradiated and scattered by the target. If the time at which the stimulation signal is generated is known (and used as a reference) and the location of the stimulation transducer is known and the location of each of the sensors is known, then the location of the target may be determined relative to that of the sensors.

The intensity of the received signals (measured by their relative amplitudes) can also be used to form an image of the target (or a distribution of targets) if the stimulation signal is scanned in space (i.e., mechanically or electronically) and the intensity of the received signals is plotted as a function of scan position. This approach, however, does not make use of the additional information present in the phase of the received signals. A robust method for both detecting and locating the target that makes use of the phase information received by the sensors is described in the present invention.

The location of the source of radiation is mathematically equivalent to finding the point of intersection between a number of ellipsoids, each of which has one focus located at the stimulating ultrasound transducer, the other focus centered on a particular sensor, and a major diameter determined by the phase shift of the signal received by that sensor relative to the stimulation waveform. This phase shift corresponds to the time between the generation of the ultrasonic stimulation signal and the reception by the sensor of a signal selected from the group consisting of reflected, demodulated, reradiated and scattered by the target. The approach used here to locate the source is to optimize a cost function. In an effort to locate the target for a given stimulation ultrasound transducer position and sensor array configuration, one could determine the position x (where x denotes a vector in three dimensions) of the target which, overall, best explains the signal/s received by the sensors. For each sensor, there is the following relation:

$$|x - p_1|_2 + |x|_2 = c\Delta t_i = c\frac{\phi_i}{2\pi}T. \quad \text{Equation (1)}$$

Where, $p_i$ is the location of the sensor relative to the stimulation transducer position;

x is the position of the source relative to the stimulation transducer position;

$|x|_2$ is the distance from the ultrasound transducer (positioned at the origin) to the source;

$\Delta t_i$ is the time of propagation of sound;

T is the period of the waveform; and c is the speed of sound.

The $\|\ \|_2$ operator around $x-p_i$ and x is the 2-norm, or Euclidean norm, computed as the square root of the sum of each component squared. This is the most commonly used measure of the length of a vector. For example, $|(-3, 4-, 12)|_2=13$.

The present inventors define a cost function as follows:

$$C(x) = \sum_{i=1}^{M} \frac{\|x - p_i\|_2 + |x|_2 - c\Delta t_i|_2}{\sigma_{\phi_i}^2} \qquad \text{Equation (2)}$$

Where M represents the number of sensors. The individual contribution from each sensor is weighted by the variance of the phase.

The inventors recognize that one can also use the $\|\ \|_1$ operator or 1-norm, or Manhattan norm, computed as the sum of the absolute values of each component. An example of 1-norm is $|(-3, 4, -12)|_1=19$. The 1-norm might be used because in some cases it may yield a more robust estimator than summing squares. In addition, one may use any measurement of distance for any reason such as robustness, ease of computation, or general convenience.

The best estimate for x is that, which minimizes the cost function. The minimum possible value of the cost function is zero, which in real terms, would correspond to locating the source exactly. In real data, however, the cost function is always greater than zero because of noise.

Therefore, the concept is to have an iterative process of systematically testing values of x against the data in order to lower the value of the cost function, until the cost function is zero or as close to zero as can be obtained. When the cost function is zero or as close to zero as possible, then the most precise value for x in the Equation (2) can be determined and that will determine the three-dimensional position coordinate of the vector x (i.e. the location of the sound source relative to the position of the sensors) so that the location of the target can be ascertained. In addition, a plot of the cost function constitutes a phase-based image of the target from one stimulation transducer position and this image may be combined with images from other stimulation transducer positions and the received signal intensity information to form compound images that are superior to the intensity image alone, the single location cost function image, and traditional B-mode ultrasonic images.

The inventors also recognize that it may be advantageous to make use of prior information regarding the location x. For example, if the transducer emits a vertical beam along the Z axis then the X-Y coordinates would be known to a high degree of accuracy. If the transducer is a focused transducer then a range of plausible values of Z would also be known. This information can be incorporated into our calculation by incorporating constraints on the values of X, Y, and Z coordinates by using constrained optimization. In the preferred embodiment, as the stimulation transducer scans a series of positions in the X-Y plane, at each X-Y coordinate we obtain signals recorded by each of the sensors. Scanning may be accomplished electronically or mechanically. From this information a cost function is used to predict the most likely location or locations of targets in the area of interest in accordance with the procedure outline above. The surface of the cost function constitutes a phase-based "snapshot" of the area of interest. The sensitivity of the cost function to the presence or absence of targets makes it a robust means of not only locating, but also detecting the targets of interest. The cost function "snapshot" at one X-Y position may be combined with "snapshots" obtained at other X-Y positions to form a compound or integrated image. The received signal intensity as a function of X-Y position may also be combined with the cost function snapshots to form a compound or integrated image. Methods of combination can include, but are not limited to summation, power averaging (RMS), weighting, and thresholding.

Figure 2:
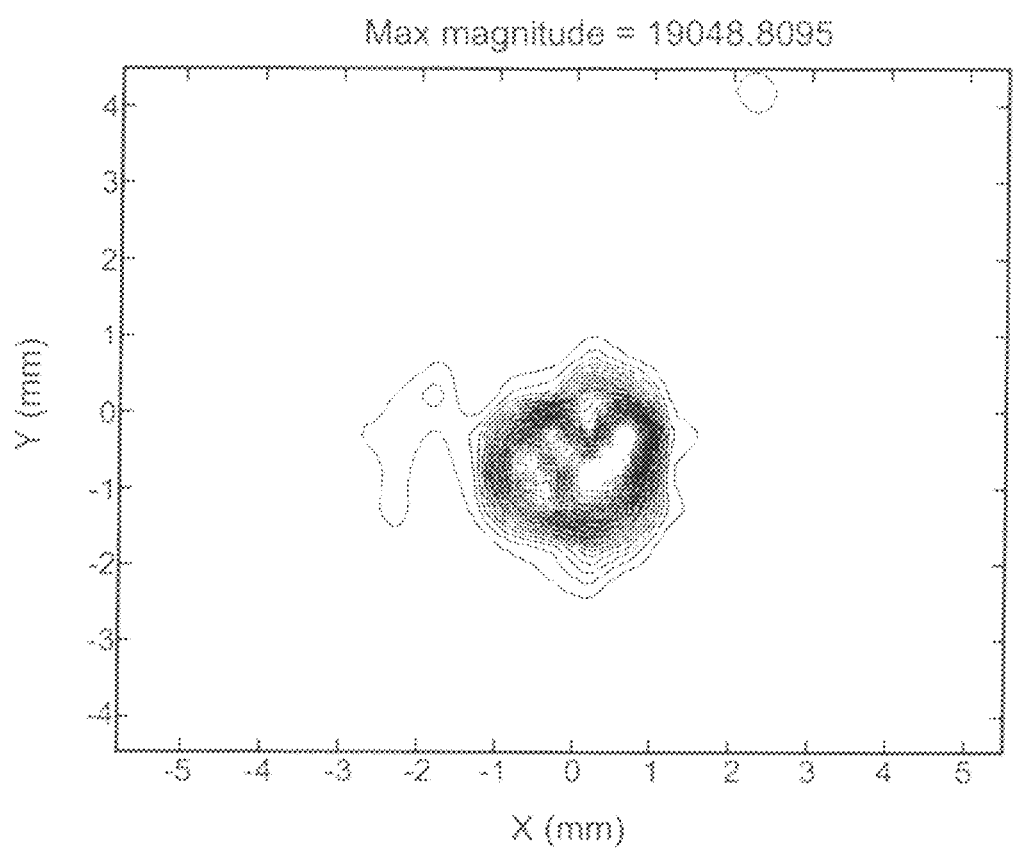
FIG. 2 is the cost function attained using the phase information recorded by six (6) sensors positioned around a 3 mm spherical target which was excited by a modulated ultrasound burst. The target is in the correct location and its dimensions are correct.

FIG. 2 shows a plot of a cost function based upon the data obtained by six (6) sensors positioned around a 3 mm diameter spherical target in water stimulated by an ultrasound signal. One can clearly see the target's location and size. In contrast, the plot of the cost function when there is no target present (not shown) is roughly four orders of magnitude different and contains only noise.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A method of detecting and locating a target comprising:
   a. positioning a multiplicity of signal receiving sensors at given locations around the target;
   b. impacting the target with an acoustic stimulation signal of at least one known frequency from a transducer which results in the generation of acoustic signals at the position of the target through processes selected from the group consisting of reflection, re-radiation, demodulation and scattering;
   c. using the sensors to receive the signals emanated at the target location due to at least one process selected from the group consisting of reflection, re-radiation, demodulation and scattering;
   d. estimation of the phases of each of the signals received by the multiplicity of sensors relative to the stimulation signal; and
   e. using a cost function to determine the presence or absence of the target and if the target is present, the likely location of the target based upon the phase estimations.

2. The method in accordance with claim 1 wherein the cost function is optimized to determine the presence or absence of the target and if the target is present, its likely location based upon the phase estimations using unconstrained optimization.

3. The method in accordance with claim 1 in which the cost function is optimized to determine the presence or absence of the target, and if the target is present, the likely location of the target based upon phase estimations using constrained optimization to incorporate additional information.

4. A method of detecting and locating a target in accordance with claim 1 in which the cost functions obtained from multiple locations of the stimulation transducer are combined to create a compound image or prediction of the presence of the target.

5. The method in accordance with claim 1, wherein the sensors are positioned around a human breast and the target is a microcalcification within the tissues of the human breast.

6. A method of detecting and locating targets comprising:
a. positioning a multiplicity of signal receiving sensors at given locations around the targets;
b. impacting the targets with an acoustic stimulation signal of at least one known frequency from a transducer which results in the generation of acoustic signals at the position of the targets through processes selected from the group consisting of reflection, re-radiation, demodulation and scattering;
c. using the sensors to receive the signals emanated at the target locations due to at least one process selected from the group consisting of reflection, re-radiation, demodulation and scattering;
d. estimation of the phases of each of the signals received by the multiplicity of sensors relative to the stimulation signal; and
e. using a cost function to determine the presence or absence of targets and if targets are present, the likely location of the targets based upon the phase estimations.

7. The method in accordance with claim 6 in which the cost function is optimized to determine the presence or absence of the targets and if the targets are present, the likely locations of the targets based upon the phase estimations using unconstrained optimization.

8. The method in accordance with claim 6 in which the cost function is optimized to determine the presence or absence of the targets and if the targets are present, the likely locations of the targets based upon the phase estimations using constrained optimization to incorporate additional information.

9. A method of detecting and locating a target or targets in accordance with claim 6 in which the cost functions obtained from multiple locations of the stimulation transducer are combined to create a compound image or prediction of the presence of the targets.

10. The method in accordance with claim 6, wherein the sensors are positioned around a human breast and the targets are microcalcifications within the tissues of the human breast.

* * * * *